(12) United States Patent
Parsons et al.

(10) Patent No.: US 6,693,179 B2
(45) Date of Patent: Feb. 17, 2004

(54) MORPHINE-6-GLUCURONIDE SYNTHESIS

(75) Inventors: Philip James Parsons, Heathfield (GB); Richard Andrew Ewin, Brighton (GB)

(73) Assignee: Cenes Limited, Cambridge (GB)

( * ) Notice: Subject to any disclaimer, the term of this patent is extended or adjusted under 35 U.S.C. 154(b) by 235 days.

(21) Appl. No.: 10/263,693

(22) Filed: Oct. 4, 2002

(65) Prior Publication Data

US 2003/0083476 A1 May 1, 2003

Related U.S. Application Data

(62) Division of application No. 09/700,909, filed as application No. PCT/GB99/01777 on Jun. 4, 1999.

(30) Foreign Application Priority Data

Jun. 6, 1998 (GB) .............................................. 9812097
Jan. 15, 1999 (GB) .............................................. 9900833

(51) Int. Cl.$^7$ .............................................. C07H 15/24
(52) U.S. Cl. ..................... 536/18.1; 536/17.4
(58) Field of Search ................ 536/17.4, 18.1

(56) References Cited

FOREIGN PATENT DOCUMENTS

| WO | WO 93/03051 | * | 2/1993 |
| WO | WO 93/05057 | * | 3/1993 |
| WO | WO 96/28451 | * | 9/1996 |

OTHER PUBLICATIONS

An improved synthesis of Beta–Glucosiduronic acid derivatives:, Jotscho Vlahov et al., Liebigs Ann. Chem. (1983), (4), 570–4, XP002123583, p. 571.*
"Synthesis of oligosaccharides related to the HNK–1 antigen . . . actopyranoside" Kornilov A.V. et al., Russ. J. Bioorg. Chem., vol. 23, No. 8, 1997, pp. 655–666, XP000856215.*
Synthesis, Opiod Receptor Affinity, and Enzymatic Hycrolysis of Stericaly Hindered Morphine 3–esters:, Christian Mignat et al., J. Pharm. Sci. (1996), 85(7), 690–694, XP002123584, see table 1, compound 10.*
A comparison of acid–base properties of substituted pyridines and their N–oxides in propylene carbonate:, Alicia Wawrzynow et al., J. Chem. Thermodyn (1998), 30(6), 713–722, XP000856067.*
A Synthesis of Morphine–6–Glucuronide:, C. Lacy et al., Tetrahedron Letters, vol. 36, No. 22, 1995, pp. 3949–3950, XP00616116, ISSN: 0040–4039, p. 3949, p. 3950, compound 1.*
"Metabolism of Drugs. LX.1) The Synthesis of Codeine and Morphine Glucuronides 2)", Hidetoshi Yoshim;ura et al., Chemical and Pharmaceutical Bulletin, JP, Tokyo, vol. 16, No. 11, 1968, pp. 2114–2119, XP000614807.*

* cited by examiner

*Primary Examiner*—Peter O'Sullivan
(74) *Attorney, Agent, or Firm*—Finnegan, Henderson, Farabow, Garrett & Dunner, L.L.P.

(57) ABSTRACT

The invention provides a novel method for synthesizing Morphine-6-Glucuronide comprising the step of reacting 3-O-pivaloyloxymorphine and methyl 1α,2-ethylorthopivalate-3,4-di-O-pivaloylglucouronate.

1 Claim, 2 Drawing Sheets

A reaction scheme according to the invention for synthesising M6G

MORPHINE-6-GLUCURONIDE SYNTHESIS

This is a divisional of Application Ser. No. 09/700,909, filed Mar. 9, 2001 which is a 371 of PCT/GB99/01777, filed Jun. 4, 1999, all of which are incorporated herein by reference.

The invention provides a novel method for synthesising Morphine-6-Glucuronide (M6G) and intermediates therefor.

Synthesis of M6G from 3-acetyl morphine and methyl 2-α-bromo-3,4,5-tri-O-acetylglucuronate is described by Lacy, C., et al. (*Tetrahedron Letters*, 36 (22), (1995), 3949–3950).

Hidetoshi, Y. et al., (*Chemical and Pharmaceutical Bulletin*, JP, TOKYO, 16 (11), (1968), 2114–2119) describe synthesis of M6G by reaction of 3-acetyl-morphine with a bromo derivative of glucuronic acid to form a Methyl [3-acetyl-morphine-6-yl -2,3,4-tri-O-acetyl-β-D-glucopyranosid] uronate intermediate which is subsequently hydrolysed to M6G.

WO 93/05057 discloses preparation of M6G by reaction of 3-acetyl morphine with methyl 1α-bromo, 1-deoxy, 2,3, 4-tri-O-acetyl D glucopyranuronate and subsequently hydrolysing the resulting intermediate to M6G.

In order to synthesise M6G the major problem to overcome is to obtain the glycoside linkage with very high β-selectivity since prior methods produce the α-anomer.

One method for obtaining high β-selectivity is to use trichloroimidate as the leaving group, as shown in WO 93/03051: FIG. 1 (Salford Ultrafine Chemicals and Research Limited).

Orthoesters are simple to synthesise from their respective bromides. There is a reaction reported in the literature[2] between the glucuronate orthoester (2) and the sugar derivative (3) catalysed by lutidinium perchlorate[3] (4) (Scheme 1).

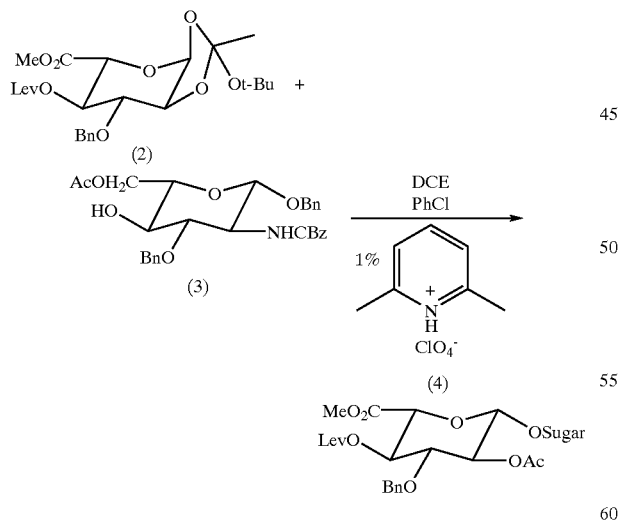

When this reaction was repeated with the t-butyl orthoacetate (5) and cyclohexanol (6 equivalents), the desired product (6) was isolated in 9% yield. Two other products also suggested that they were the desired product, but with the loss of one acetyl group, isolated in a combined yield of 43% (Scheme 2).

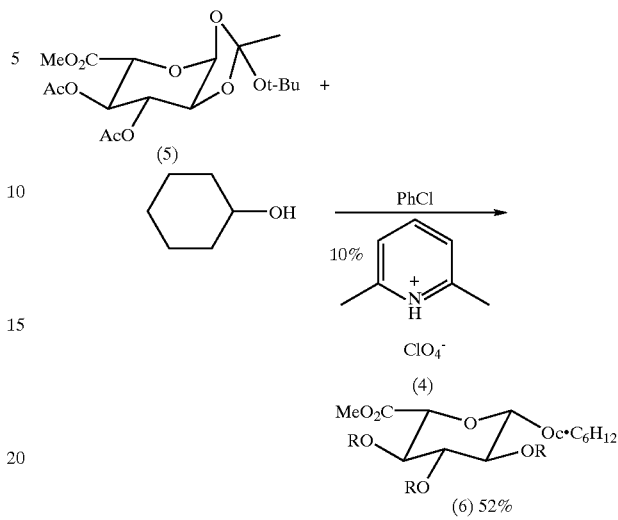

When 1.2 equivalents of 4-tert-butylcyclohexanol was used, the desired compound (7) was obtained in 17% yield. Other compounds obtained from the reaction also appeared to contain the desired peaks in the nmr, but after further examination proved to be the product of transorthoesterification (8) (Scheme 3).

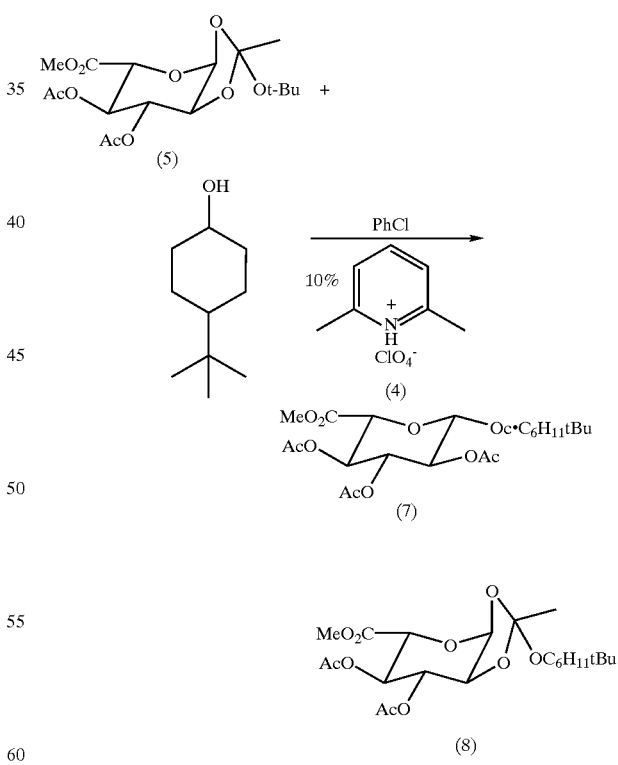

Reaction of Orthoester (5) with Protected Morphine

Initially, 1.2 equivalents of 3-TBS protected morphine and the orthoester (5) were dissolved in chlorobenzene and half of the solvent was distilled off before 0.1 equivalents of lutidinium perchlorate (4) in chlorobenzene was added. The solvent was continuously distilled off while fresh solvent was added, and after 2.5 h another compound was formed with similar tlc properties to the protected morphine. Workup and chromatography gave a compound which corresponded to trans-orthoesterified material (9). None of the desired material was obtained (Scheme 4).

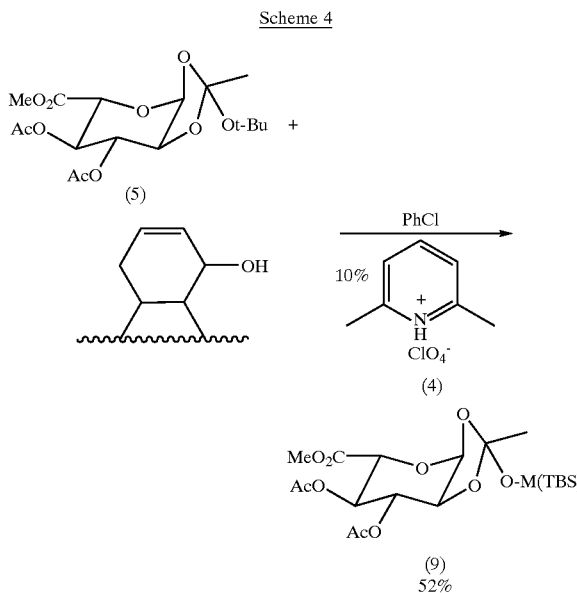

This product (9) was resubmitted to the reaction conditions (0.1 equivalents of lutidinium perchlorate and protected morphine in refluxing chlorobenzene) with no new products formed after 4 h. Two further reactions were attempted using two equivalents of orthoester (5) and 0.2 equivalents of lutidinium perchlorate and 1 equivalent of orthoester (5) and 1.2 equivalents of lutidinium perchlorate, but both gave varying yields of orthoester (9).

We have concluded that a different, more bulky, alkyl group was needed on the orthoester to hinder attack there. Initially, the isopropyl group was examined. However, the initial reaction, perisobutyrylation, failed to give a compound which recrystallised from petrol, so the α and β anomers could not be separated. Therefore, attention focussed on the pivaloyl group.

Figure 1:
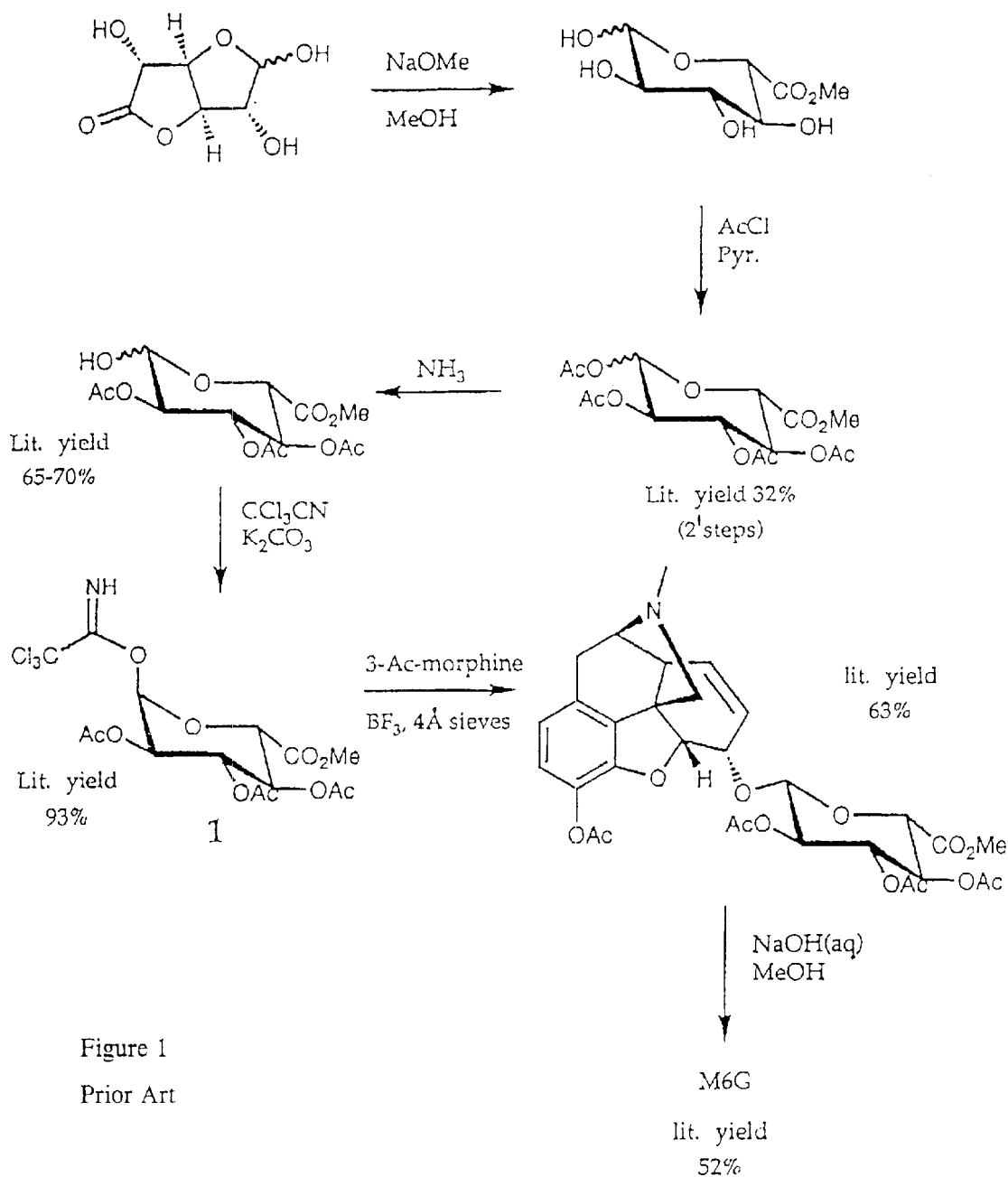
FIG. 1 is a prior art process.
Figure 2:
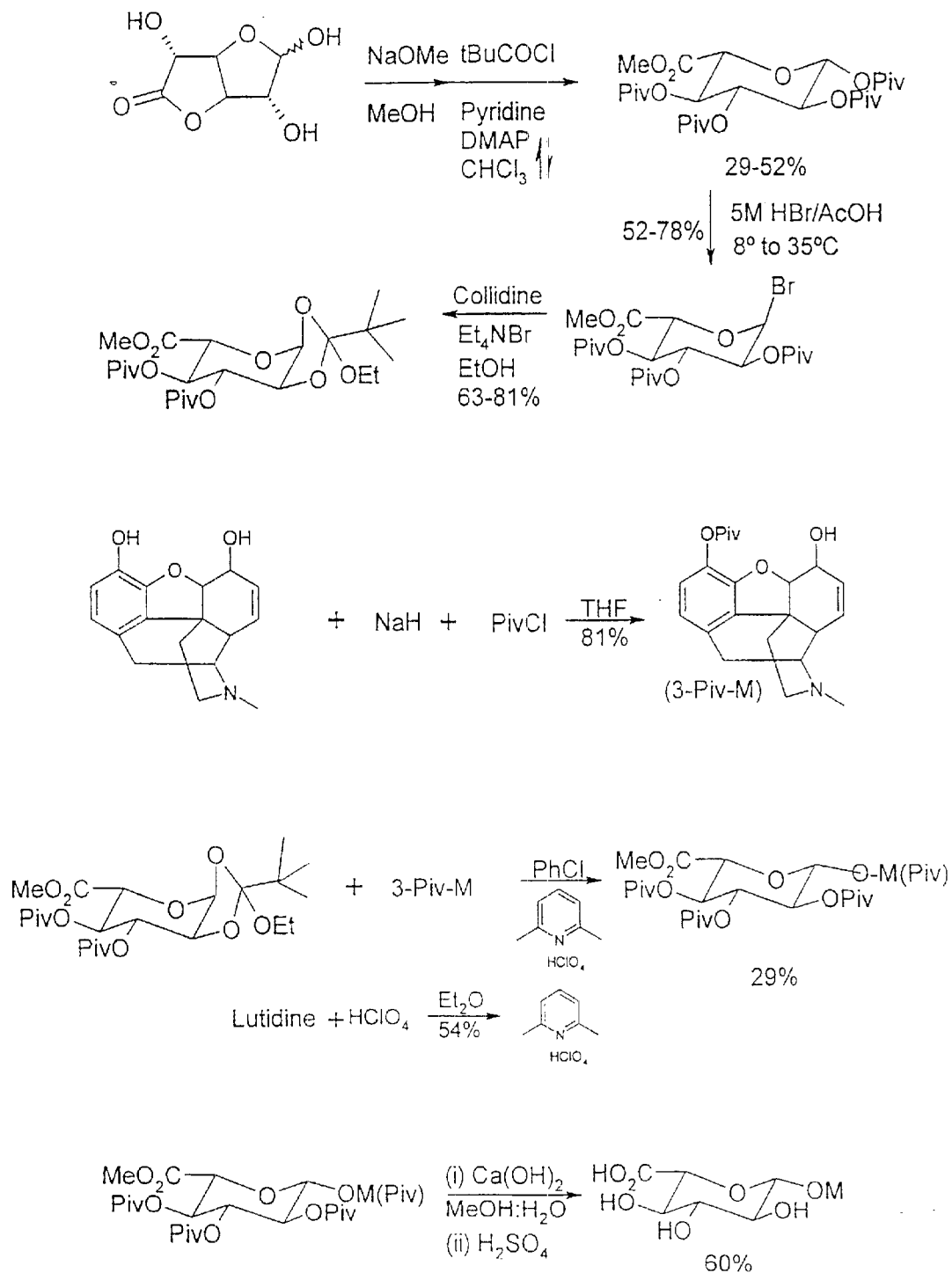
FIG. 2 is a reaction scheme according to the invention for synthesizing M6G.

The invention is further described with reference to the accompanying FIG. 2 which shows a summary of a reaction scheme according to the invention for synthesising M6G.

Synthesis of the Perpivalated Glucuronide

Synthesis of perpivalated glucuronide proved troublesome at first, giving a mixture of 3 and 4 non-pivalated material (scheme 5).

Scheme 5

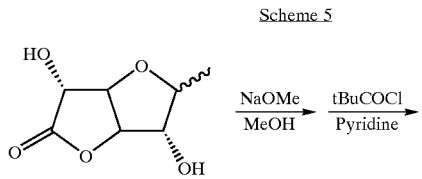

-continued

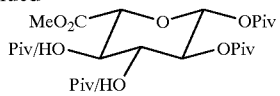

A search through the literature revealed that glucose can be perpivalated by heating the reaction to reflux for 3 h. and then stirring it for 7 days.

When this reaction was repeated on ring-opened glucurono-3,6-lactone (Scheme 6), perpivalated product (10) was obtained by crystallisation of the crude product from MeOH (or EtOH) and water and drying the crystals by dissolving them in DCM, separating any water present, drying, and then evaporating the organic layer to give the product in 29–52% yield, a substantial improvement on previous yields for this step.

Scheme 6

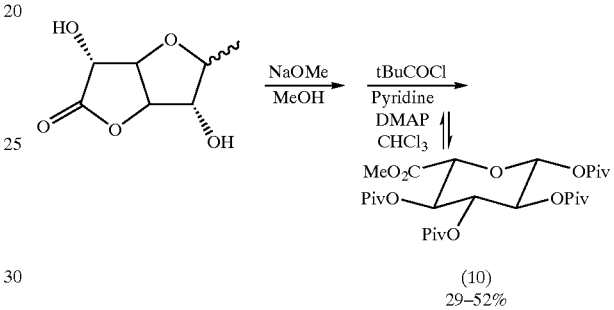

DMAP was added to aid perpivalation, although there has been no evidence to suggest that this is necessary. The variation in the yields quoted is probably due to the amount of MeOH left over from the first step. The high yield quoted (52%) was obtained by using 6 (instead of 5) equivalents of tBuCOCl. A slight colouration of the final product proved no handicap in the next step, as after a silica plug and recrystallisation, pure white crystals were obtained.

Synthesis of the Orthoester (6)

Conversion of the perpivalated material (10) to the α-bromide (11) required gentle heating (to approxiamately 35° C.) to dissolve the substrate in the reaction mixture. The reaction proceeded very cleanly by tlc analysis, showing a spot to spot conversion. Attempts to reduce the amount of HBr used to five equivalents led to incomplete conversion of the starting material, so 12 equivalents were used as before. The product was slowly crystallised from EtOH/water or MeOH/water to give long white crystals in a yield of 52–78%. High yields were always obtained when fresh HBr/AcOH was used. The crystals were dried by again dissolving them in dichloromethane, the water separated, and the organic layer dried and evaporated.

The orthoester (12) was obtained in 63–81% yield by stirring a 1:1 mixture of EtOH:collidine at 70° C. (oil bath temperature) with the bromide (11) and 0.8 equivalents of Et$_4$NBr (Scheme 7). The product can easily be crystallised from EtOH/water water or MeOH/water as white crystals, with a trace of collidine still present (detected by smell!) but which doesn't effect the next reaction. An interesting by-product from this reaction (obtained in about 10%) is the result of EtOH attacking the anomeric position to give the β-anomer (13) Again, the difficulty in drying the crystals meant that they were dissolved in petrol (40–60), the water separated, and the organic layer dried and evaporated.

Scheme 7

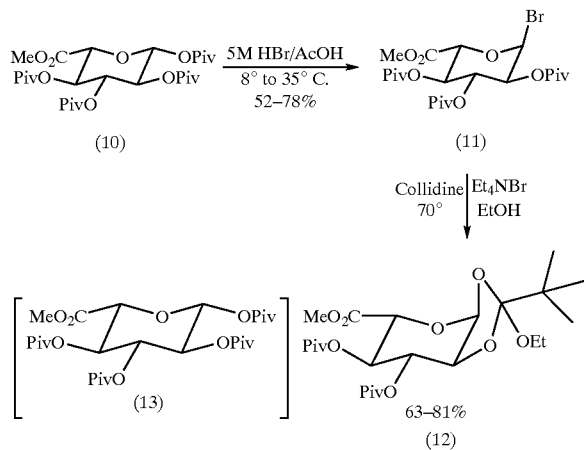

Synthesis of 3-Pivalated Morphine (14)

Selective deprotonation of the phenolic OH of morphine was achieved using NaH (surprisingly, the anion turns out to be soluble in THF) and trimethylacetyl chloride was added dropwise to give the desired product after recrystallisation from MeOH/water (Scheme 8). Again, the difficulty in drying the crystals meant that they were dissolved in dichloromethane, the water separated, and the organic layer dried and evaporated to give a white powder in 81% yield.

Scheme 8

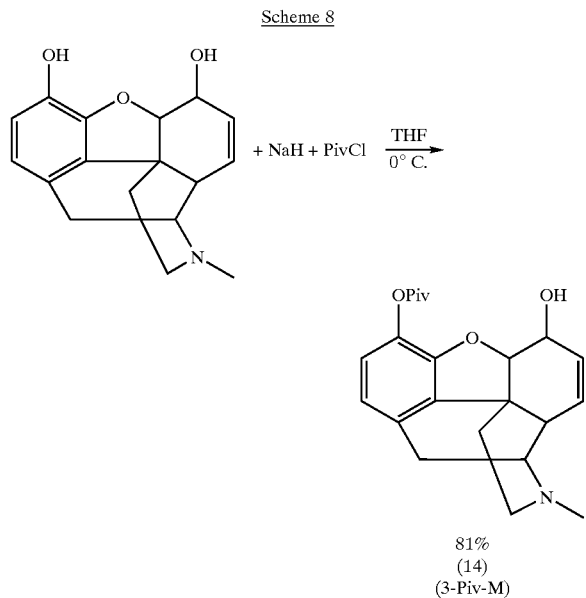

1.1 equivalents of trimethylacetyl chloride were used, but this led to some dipivalated morphine which proved difficult, to recrystallise apart from mono-pivalated morphine (14) or the protected M6G (16). Thus, it would be advantagous in the future to use 1 equivalent of trimethylacetyl chloride.

Synthesis of Lutidinium Perchlorate (15)

This was achieved by simply adding aqueous perchloric acid to an ether solution of lutidine (excess, as this remains in the Et$_2$O layer) (Scheme 9) and evaporating the water until crystals form, which were collected by filtration.

Scheme 9

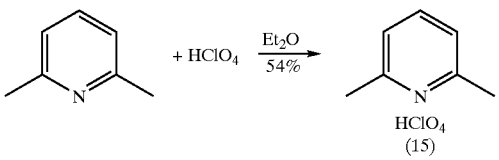

The crystals are deliquescent and thus need to be dried under high vacuum prior to use.

Other acid catalysts have been investigated in the coupling reaction below, but with no success. However, this compound has shown no tendencies to decompose, proving both thermal and shock stable, so shouldn't prove a problem on scale up.

Coupling of the Orthoester (12) with 3-pivalated Morphine (14)

Coupling the orthoester (12) to 1.1 equivalents of 3-pivalated morphine (14) was achieved by adding 0.1 equivalents of lutidinium perchlorate (15) every 15 min. until 1.2 equivalents had been added to the distilling chlorobenzene. The reaction was then stirred under reflux for a further 2 h to give a mixture of 3-pivalated morphine (14) protected M6G (16) and much less polar materials. Work-up and crude purification by chromatography gave protected M6G (16) and 3-pivalated morphine (14) which was purified by recrystallisation from MeOH/(water, small quantity) to give (16) in 29% yield (with no detectable quantity of α-anomer or trans-orthoesterified material from nmr analysis) (Scheme 10).

Scheme 10

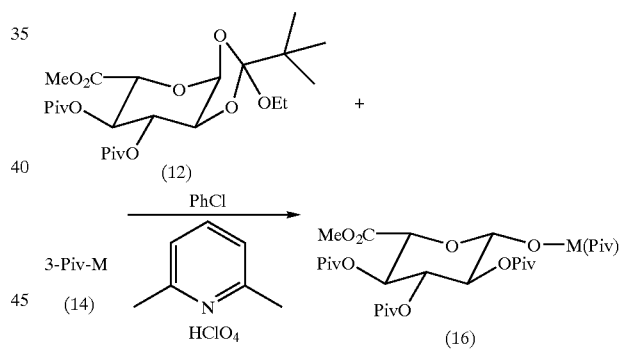

This yield is the greatest amount obtained from this reaction and further improvements might be possible. Lutidinium perchlorate (15) was added every 15 min. as a solid appeared to crystallise from the reaction mixture (presumably the 3-pivalated morphine perchlorate) and, if no more catalyst is added, the major product turned out to be the trans-orthoesterified material (similar to orthoester (9) in Scheme 14). If 1.2 equivalents of lutidinium perchlorate (15)was added directly to the reaction, only 6% of coupled material was obtained (presumably as all the 3-pivalated morphine had been removed from the reaction as the perchlorate salt). The main problem with adding the catalyst, is its insolubility in chlorobenzene lower than approxiamately 100° C. If it is possible on a large scale to add lutidinium perchlorate (15) in chlorobenzene at 100° C., this may prove not only simpler to add the catalyst, but also lead to increasing yields. The reaction also needs to be refluxed for an additional 2 hours after all the lutidinium perchlorate (15)

has been added, to cause the trans-orthoesterified material to rearrange to the desired material.

Global Deprotection of Protected M6G (16)

Heating protected M6G (16) in MeOH until it dissolves before adding the water (which causes it to crystallise from the reaction mixture) and Ca(OH)$_2$ seems to be the mildest way of performing this reaction. After stirring for 3 days, the reaction gave, by tlc analysis, M6G (17) and morphine (Scheme 11).

Scheme 11

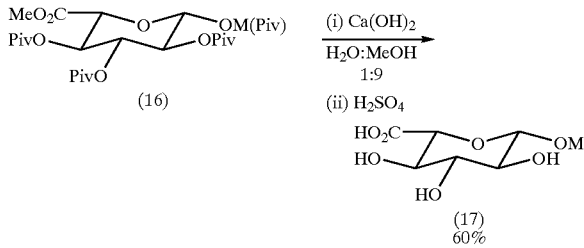

The reaction was quite slow due to the insolubility of Ca(OH)$_2$ in water, but when the reaction is deemed to have finished by tlc analysis, 6.5 equivalents of sulfuric acid were added or until the reaction reached pH 4. The CaSO$_4$ so formed was filtered off and the trimethylacetic acid also formed was removed by washing the filtrate with DCM. Evaporating the water proved the hardest part of this reaction due to excessive foaming. Some CaSO$_4$ remains in the filtrate and this was removed by adding MeOH to crystallise it out. The residue produced after all the water had been evaporated was purified by repeated washing with MeOH as M6G is virtually insoluble in MeOH while morphine is soluble in it. The morphine present in the crude residue probably arrived there due to the di-pivalated morphine passing through the coupling reaction and then being deprotected to morphine in this final step. Hopefully, by using strictly 1 equivalent or trimethylacetyl chloride, this should eliminate the di-pivalated morphine, thus make purification of M6G even simpler, and increasing the yield for the final step.

The invention is further described in detail below by way of example only.

EXAMPLE 1

Methyl 1β,2,3,4-tetra-O-pivaloylglucuronate

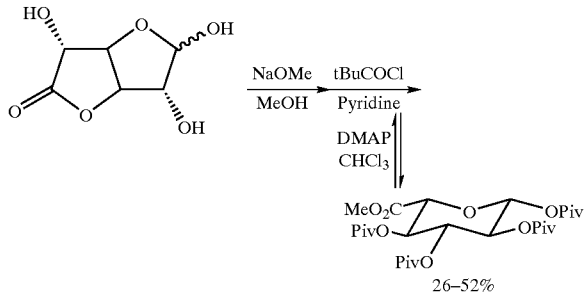

Glucurono-6,3-lactone (147 g, 0.8 mol) was stirred as a suspension in methanol (1 L, not dried) under nitrogen. A catalytic amount of sodium methoxide (147 mg, 2.6 mmol) was added to the suspension, and after 2 hours most of the suspension was still present. The reaction proceeded very slowly at room temperature, ~18° C., but noticeably increased in rate when the reaction was warmed, therefore, the reaction was gently warmed to ~25° C. After another hour of stirring, most of the suspension had dissolved to leave a clear yellow solution that was then evaporated. The residue was found to be a solid, which tended to foam under vacuum, which made total removal of all the methanol difficult.

Chloroform (400 mL), followed by 6 equivalents of pyridine (400 mL, 4.8 mol) and a catalytic amount of N,N-dimethyl-4-aminopyridine (4 g) was then added to the residue that slowly dissolved in this mixture. The solution was stirred using a magnetic stirrer plate and flea, but the problems encountered in continuously stirring this reaction would make an overhead mechanical stirrer preferable at this stage. The reaction was then cooled to 0° C. and 5 equivalents of trimethylacetyl chloride (500 mL, 4 mol) was added gradually, not allowing the reaction to warm to a temperature above ~8° C. The yellow/orange solution became colourless on addition of the first portion of trimethylacetyl chloride, and after approximately half of the volume was added, a white precipitate was observed (pyr.HCl). After addition was complete, the reaction was stirred overnight at room temperature before being heated at reflux for 2 hours, during which time the reaction turned black with the white precipitate still present. Tlc analysis showed that the desired product had been produced (Rf 0.5, 1:1 Et$_2$O:petrol), but some mono-unprotected material remained (Rf 0.3 and 2.8, 1.1 Et$_2$O:petrol). The reaction was then allowed to cool to room temperature over 3 hours, then further cooled to 0° C. before methanol was added gradually (this quenches the excess trimethylacetyl chloride to give methyl trimethylacetate, which is evaporated off with the solvent). The black solution was then poured into a 2 L separating funnel, and washed with water (600 mL), 1M HCl (2*600 mL), water (600 mL), and saturated aqueous NaHCO$_3$ (2*600 mL). The organic layer was then dried with MgSO$_4$ and passed through approximately 5 cm of silica on a sinter funnel (which removed a black baseline compound). The silica was washed with dichloromethane (100 mL) and the combined filtrates evaporated to leave a black viscous oil, which was re-dissolved in ethanol (~1 L) and had water added until the solution turned turbid (~500 mL). More ethanol was added until the turbid solution cleared, and the solution was left to crystallise overnight. The yellow crystals were dissolved in dichloromethane (300 mL) and any excess water removed by separation, the dichloromethane layer Was then dried and evaporated.

The white powder (113.5 g, 26%) was then used in the next reaction.

Methyl 1-deoxy-1-α-bromo,2,3,4-tri-O-pivaloylglucuronate

Methyl 1(β),2,3,4-tetra-O-pivaloylglucuronate (108.5 g, 0.2 mol) was dissolved in glacial acetic acid (500 mL) (with the aid of some gentle heating) and placed in a bath of cold water. 12 equivalents of 33% HBr in acetic acid (500 mL, 2.9 mol) were then added at a rate required to prevent the acetic acid freezing without the reaction exotherming too greatly. After the addition was complete, the reaction was allowed to warm to room temperature. If any white solid (starting material) persisted, gentle warming was applied to the reaction until it dissolved and the reaction then allowed to cool and stir overnight. The orange/brown solution was then cautiously poured into dichloromethane (500 mL)/water (500 mL), the organic layer separated, washed with water (500 mL) and saturated NaHCO₃ (500 mL) (with care to avoid too rapid an evolution of $CO_2$). The organic layer was then dried (MgSO₄) and passed through approximately 2 cm of silica, the silica was washed with more dichloromethane (50 mL) and the combined filtrates evaporated (taking care to remove all the dichloromethane). The residue was then dissolved in EtOH (~400 mL) and water added until the reaction turned turbid. More ethanol was added until the solution just turned clear and the product allowed to crystallise overnight which were collected by filtration. The crystals were dissolved in dichloromethane and the organic layer separated from any water that remained, dried (MgSO₄), and evaporated.

The white powder (76 g, 72%) was then used in the next reaction.

Methyl 1α,2-ethylordhopivalate-3,4-di-O-pivaloylglucuronate

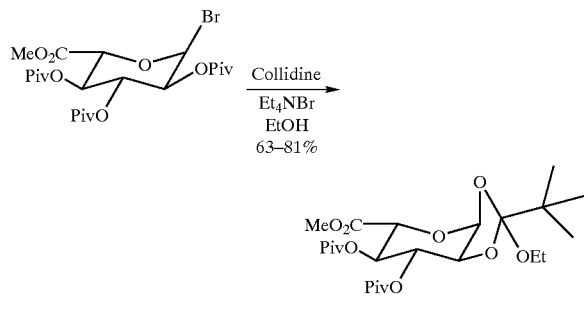

Methyl 1-deoxy-1-α-bromo,2,3,4-tri-O-pivaloylglucuronate (69 g, 0.13 mol) was dissolved in collidine (300 mL) (pre-dried by distilling onto activated 3 Å sieves) and ethanol (300 mL) (pre-dried by distilling from NaOEt onto activated 3 Å sieves). 0.8 equivalents of pre-dried tetraethylammonium bromide (22 g, 0.1 mol) was then added to the reaction, which was stirred at 60° C. (oil bath temperature 70° C.) overnight. The reaction was then cooled and poured into dichloromethane (500 mL)/water (500 mL) and the organic layer separated, dried (MgSO₄), and evaporated. The collidine was removed by low-pressure distillation (total evaporation is not necessary), the residue dissolved in EtOH (~400 mL), and water added until the product started to crystallise out. The white crystals were collected by filtration and dissolved in petrol. The organic layer was then separated from any water that remained, dried (MgSO₄), and evaporated.

The white powder (50 g, 78%) was then used in the next reaction

3'-O-Pivaloylmorphine

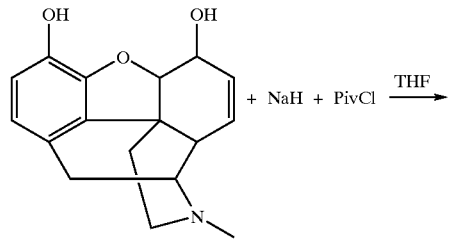

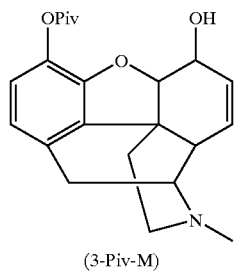

(3-Piv-M)

Morphine (12 g, 42 mmol) was added portionwise to a THF (80 mL, Na dried) suspension of 1.05 equivalents of petrol washed NaH (60% dispersion in oil, 1.768 g, 44 mmol) at 0° C. After stirring for 1 h at room temperature, 1.1 equivalents of trimethylacetyl chloride (5.7 mL, 46 mmol) were added to the clear reaction mixture at 0° C. and eventually a white solid precipitated from the reaction. After 1 h⁻., MeOH⁻ (10 mL) followed by saturated aqueous sodium bicarbonate (100 mL) were added to the reaction which was then extracted with Et₂O (2×200 mL). The combined extracts were washed with brine (200 mL), dried, and evaporated. The residue was recrystallised from MeOH/water and the crystals dissolved in dichloromethane and the organic layer separated from any water that remained, dried (MgSO₄), and evaporated.

The white powder (12.6 g, 81%) was then used in the next reaction.

Lutidinium Perchlorate

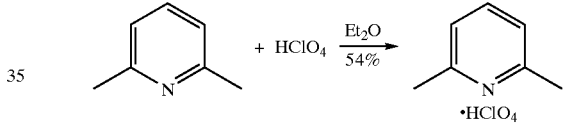

A 60% aqueous solution of perchloric acid (29 mL, 0.27 mol) was added to 1.1 equivalents of lutidine (34 mL, 0.29 mL) in Et₂O (250 mL) at 0° C. After stirring for 0.5 h. at room temperature, the aqueous layer was separated and the water evaporated until a white solid crystallised from the water, the crystals filtered off and washed with Et₂O to give the product as a white crystalline solid (30 g, 54%). The product was dried under high vacuum prior to use.

Methyl 1β-6'-O-(3'-O-pivaloylmorphine)-2,3,4-tri-O-pivaloylglucuronate

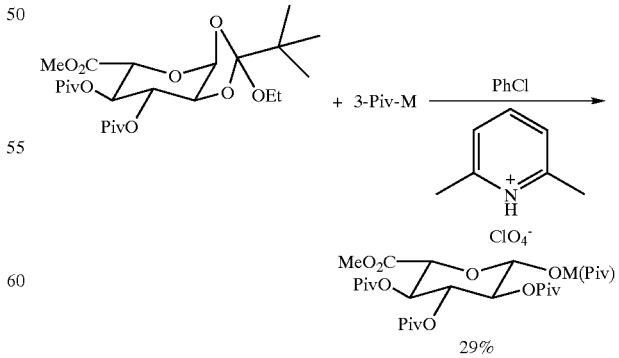

A chlorobenzene (400 mL) (distilled from CaH₂ onto activated 3 Å sieves) solution of 1.1 equivalents of 3-O-pivaloyoloxymorphine (8.49 g, 23 mmol) and methyl 1α,2- ethylorthopivalate-3,4di-O-pivaloylglucuronate (10 g, 20 mmol) was heated to reflux to distil off approximately half of the solvent. 0.1 Equivalents of lutidinium perchlorate (415 mg, 2 mmol) was then added to the reaction that was still at reflux. The reaction was then stirred at reflux for 15 min with chlorobenzene continuously distilled off and fresh chlorobenzene added. After this time, a further 0.1 equivalents of lutidinium perchlorate (415 mg, 2 mmol) was then added to the reaction. This procedure was repeated every 15 min until 1.2 equivalents of lutidinium perchlorate (5.2 g, 25 mmol) had been added. The reaction was then stirred at reflux for 2 hours with chlorobenzene continuously distilled off and fresh chlorobenzene added. After this time, the reaction was allowed to cool and then poured into dichloromethane (500 mL)/water (500 mL), the organic layer separated, washed with saturated aqueous sodium bicarbonate (500 mL), dried, and evaporated. The residue, after some of the chlorobenzene had been removed under low pressure, was applied to the top of a silica column and eluted with diethyl ether to remove the non-polar by-products and then with 5% methanol in dichloromethane. The desired product was separated from 3-Piv-M by recrystallisation from MeOH/water to give a white crystalline powder (4.76 g, 29%).

Morphine-6-gluconoride

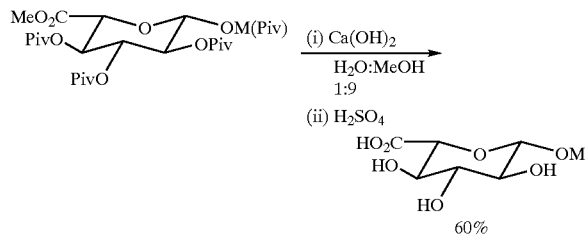

Methyl 1β-6'-O-(3'-O-pivalayloxymorphine)-2,3,4-tri-0-pivaloylglucuronate (3.06 g, 3.77 mmol) was dissolved in MeOH (60 mL) (with the help of some heating) and had water (7 mL) followed by 6.5 equivalents of calcium hydroxide (1.817 g, 24.5 mmol) added to it. The reaction was stirred for two days when water (60 mL) was added and the reaction stirred for a further day until the reaction was shown to be complete by tic analysis (Rf 0.3, 45% nBuOH; 15% water; 20% acetone; 10% acetic acid; 10% of a 5% aqueous solution of ammonia). 6.5 equivalents of 0.25M aqueous sulphuric acid (98 mL, 24.5 mmol) were added (pH 4) and the reaction stirred for 1 hour. The reaction was then filtered to remove $CaSO_4$ and the solid washed with water (30 mL). The filtrate was then washed with DCM (2×100 mL), three quarters of the water evaporated and the same quantity of MeOH added. The white solid (mainly $CaSO_4$) was then filtered and the filtrate evaporated. The residue (1.56 g) had MeOH (100 mL) added and the white solid filtered and repeatedly washed with MeOH to give the desired compound (1.05 g, 60%) which could, according to the literature, be recrystallised from $H_2O$/MeOH (although this has not been performed on this material).

References

1. For a review of orthoesters and their synthetic applications see N. K. Kochetkav and A. F. Bochkov, *Recent Developments in the Chemistry of Natural Carbon Compounds*, Ed. R. Bognár, V. Bruckner, and Cs. Szántay, Akadémiai Kiadó: Budapest, 1971, vol. 4, p.77 191.
2. H. P. Wessel, L. Labler, and T. S. Tschopp, *Helv. Chim. Acta.*, 1989, 72, 1268.
3. The use of 2,6-dimethylpyridinium perchlorate (4) was first reported by N. K. Kochetkov, A. F. Bochkov, T. A. Sokolovskaya, and V. J. Snyatkova, *Carbohydr. Res.*, 1971, 16, 17.

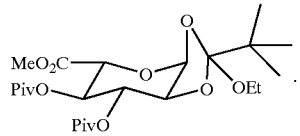

What is claimed is:

1. A compound or derivative thereof of the following formula: